United States Patent [19]

Ondetti

[11] 4,127,729

[45] Nov. 28, 1978

[54] AMINO ACID DERIVATIVES

[75] Inventor: Miguel A. Ondetti, Princeton, N.J.

[73] Assignee: E. R. Squibb & Sons, Inc., Princeton, N.J.

[21] Appl. No.: 879,409

[22] Filed: Feb. 21, 1978

Related U.S. Application Data

[62] Division of Ser. No. 747,282, Dec. 3, 1976, Pat. No. 4,091,024.

[51] Int. Cl.$^2$ .................. C07C 149/23; C07C 153/07
[52] U.S. Cl. ............................. 560/147; 260/455 R; 260/465.4; 562/556
[58] Field of Search .................... 560/147; 260/534 E, 260/534 G, 534 L, 534 M, 534 S, 455 R, 465.4

[56] References Cited

U.S. PATENT DOCUMENTS

| | | | |
|---|---|---|---|
| 2,723,972 | 11/1955 | Herrick | 560/16 |
| 3,246,025 | 4/1966 | Mita | 260/534 S |
| 3,517,089 | 6/1970 | Newallis | 260/942 |
| 3,971,828 | 7/1976 | Mita | 260/534 S |
| 4,046,889 | 9/1977 | Ondetti | 260/293.85 |
| 4,053,651 | 11/1977 | Ondetti | 260/534 S |
| 4,081,399 | 3/1978 | Dear | 260/534 S |

FOREIGN PATENT DOCUMENTS

| | | | |
|---|---|---|---|
| 2,709,820 | 9/1977 | Fed. Rep. of Germany | 260/534 S |
| 1,491,204 | 8/1967 | France | 260/534 S |

*Primary Examiner*—James O. Thomas, Jr.
*Assistant Examiner*—Michael Shippen
*Attorney, Agent, or Firm*—Lawrence S. Levinson; Merle J. Smith

[57] ABSTRACT

New derivatives of amino acids which have the general formula

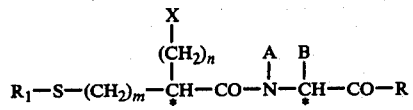

are useful as angiotensin converting enzyme inhibitors.

10 Claims, No Drawings

AMINO ACID DERIVATIVES

This is a division, of application Ser. No. 747,282, filed Dec. 3, 1976, now U.S. Pat. No. 4,091,024.

SUMMARY OF THE INVENTION

This invention relates to new derivatives of amino acids which have the general formula

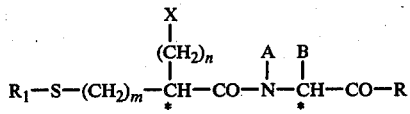
(I)

and salts thereof,
wherein
R is hydroxy or lower alkoxy;
$R_1$ is hydrogen, lower alkanoyl, benzoyl or

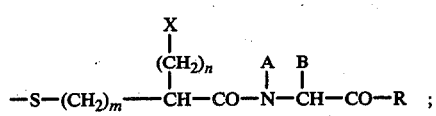

A is hydrogen, lower alkyl or hydroxy-lower alkylene; B is hydrogen, lower alkyl, phenyl, phenyllower alkylene, hydroxy-lower alkylene, hydroxyphenyl-lower alkylene, amino-lower alkylene, guanidino-lower alkylene, mercapto-lower alkylene, lower alkyl-thio-lower alkylene, imidazolyllower alkylene, indolyl-lower alkylene, carbamoyllower alkylene or carboxy-lower alkylene, or A and B together form a $(CH_2)_p$ bridge which completes a ring of 5 or 6 atoms with the nitrogen and carbon to which they are joined, one carbon optionally bearing a hydroxy group;
X is carboxy, lower alkoxycarbonyl, carbamoyl, N-substituted carbamoyl or cyano;
m is 0 or 1;
n is 0, 1, 2, 3 or 4; and
p is 3 or 4. The asterisks denote centers of asymmetry.

DETAILED DESCRIPTION OF THE INVENTION

. The invention includes substituted derivatives of amino acids having formula I above.

Compounds in the group represented by formula I which are derived from or include the structure of the amino acids glycine, alanine, leucine, threonine, phenylglycine, phenylalanine, lysine, arginine, glutamine, histidine, methionine, serine, cysteine, tyrosine, valine, asparagine, glutamic acid, proline, hydroxyproline, or tryptophane are broadly preferred. Preferred modifications are compounds of formula I wherein R is hydroxy; $R_1$ is hydrogen or lower alkanoyl (particularly hydrogen or acetyl);

X is lower alkoxycarbonyl or carbamoyl; A is hydrogen or joins in a 5- or 6-membered ring with B, especially a 5-membered ring; B is lower alkyl, amino-lower alkylene or phenyl-lower alkylene or joins in a ring with A, especially a 5-membered ring; m is 1; and n is 1 or 2.

Especially preferred are those compounds of formula I which are derived from proline and have the formula

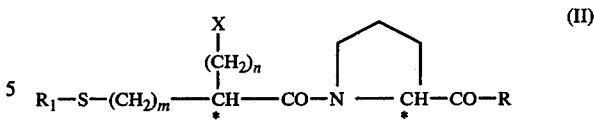
(II)

The symbols have the same preferred meanings described above.

The lower alkyl groups represented by any of the variables include straight and branched chain hydrocarbon radicals from methyl to heptyl, for example, methyl, ethyl, propyl, isopropyl, butyl, isobutyl, t-butyl, pentyl, isopentyl and the like. The lower alkylene groups are of the same kind also having 1 to 7 carbons. Similarly, the lower alkoxy groups are of the same kind with a link to oxygen, for example, methoxy, ethoxy, propoxy, isopropoxy, butoxy, isobutoxy, t-butoxy and the like. The $C_1$-$C_4$ members, especially $C_1$ and $C_2$ members, of all types are preferred. Phenylmethyl is the preferred phenyl-lower alkylene group and methoxy and t-butoxy the preferred lower alkoxy groups. The lower alkanoyl groups are the acyl radicals of the lower (up to 7 carbons) fatty acids, e.g., acetyl, propionyl, butyryl and the like, acetyl being preferred.

The N-substituted carbamoyl groups represented by X are carbamoyl radicals bearing on the nitrogen a lower alkyl or a phenyl-lower alkylene substituent.

The products of formula I and the preferred subgroups can be produced by various methods of synthesis.

According to a preferred method, the amino acid of the formula

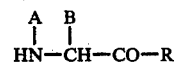
(III)

wherein A and B are defined as above, and R is hydroxy is acylated with an acid of the formula

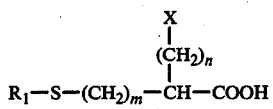
(IV)

wherein $R_1$, m and n have the meaning defined above and X is other than carboxyl, by one of the known procedures in which the acid IV is activated, prior to reaction with the acid III, involving formation of a mixed anhydride, symmetrical anhydride, acid chloride, active ester, Woodward reagent K, N,N'-carbonylbisimidazole, EEDQ (N-ethoxycarbonyl-2-ethoxy-1,2-dihydroquinoline) or the like. When R is lower alkoxy, this or other known methods of coupling such moieties can be used. [For a review of these methods, see Methoden der Organischen Chemie (Houben-Weyl) Vol. XV, parts 1 and 2 (1974)].

Compounds of formula I wherein X is —$CONH_2$ and R is hydroxy can also be produced by ammonolysis of those compounds of formula I wherein X is lower alkoxycarbonyl.

Compounds of formula I wherein m is 0 can also be produced by acylation of the acid of formula II with an acid of the formula

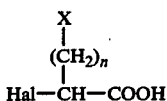
(V)

wherein Hal represents halogen, preferably chlorine or bromine, followed by displacement with a thiol acid of the formula

 (VI)

When the product obtained is an ester, e.g., $R_1$ is lower alkoxy, the ester can be converted to the free carboxy group by saponification or, when $R_1$ is a tertiary lower alkoxy group, e.g., t-but oxy, by treatment with trifluoroacetic acid and anisole. Conversely the free acid can be esterified by conventional procedures.

The disulfides of formula I, wherein $R_1$ is

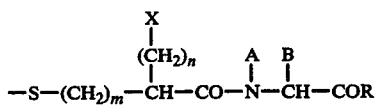

are obtained by oxidation of the compound of the formula

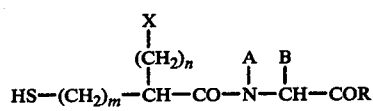 (VII)

e.g., with an alcoholic solution of iodine.

Products of formula I have two asymmetric carbon atoms. These carbon atoms are indicated by an asterisk in formula I. The compounds accordingly exist in diastereoisomeric forms or in racemic mixtures thereof. All of these are within the scope of the invention. The above described syntheses can utilize the racemate or one of the enantiomers as starting material. When the racemic starting material is used in the synthetic procedure, the stereoisomers obtained in the product can be separated by conventional chromatographic or fractional crystallization methods. In general, the L-isomer with respect to the carbon of the amino acid constitutes the preferred isomeric form.

The compounds of this invention form basic salts with various inorganic and organic bases which are also within the scope of the invention. Such salts include ammonium salts, alkali metal salts like sodium and potassium salts (which are preferred), alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. The non-toxic, physiologically acceptable salts are preferred, although other salts are also useful, e.g., in isolating or purifying the product.

The salts are formed in conventional manner by reacting the free acid form of the product with one or more equivalents of the appropriate base providing the desired cation in a solvent or medium in which the salt is insoluble, or in water and removing the water by freeze drying. By neutralizing the salt with an insoluble acid like a cation exchange resin in the hydrogen form [e.g., polystyrene sulfonic acid resin — Dowex 50 (Mikes, Laboratory Handbook of Chromatographic Methods (Van Nostrand, 1961) page 256] or with an aqueous acid and extraction with an organic solvent, e.g., ethyl acetate dichloromethane or the like, the free acid form can be obtained, and, if desired, another salt formed.

Additional experimental details are found in the examples which are preferred embodiments and also serve as models for the preparation of other members of the group.

The compounds of this invention inhibit the conversion of the decapeptide angiotensin I to angiotensin II and therefore are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance present which has been implicated as the causative agent in various forms of hypertension in various mammalian species, e.g., rats, dogs, etc. The compounds of this invention intervene in the angiotensinogen → angiotensin I → angiotensin II sequence by inhibiting angiotensin converting enzyme and reducing or eliminating the formation of the pressor substance angiotensin II.

The inhibition of the angiotensin converting enzyme by compounds of formula I can be measured in vitro with isolated angiotensin converting enzyme from rabbit lungs following the procedure described by Cushman and Cheung [Biochem. Pharmacol., 20, 1637 (1971)], and with an excised smooth muscle assay [E. O'Keefe, et al., Federation Proc. 31, 511 (1972)] in which these compounds have been shown to be powerful inhibitors of the contractile activity of angiotensin I and potentiators of the contractile activity of bradykinin.

The administration of a composition containing one or a combination of compounds of formula I or physiologically acceptable salt thereof to the species of hypertensive mammal alleviates or reduces angiotensin dependent hypertension. A single dose, or preferably two to four divided daily doses, provided on a basis of about 5 to 1000 mg. per kilogram per day, preferably about 10 to 500 mg. per kilogram per day is appropriate to reduce blood pressure. The animal model experiments described by S. L. Engel, T. R. Schaeffer, M. H. Waugh and B. Rubin, Proc. Soc. Exp. Biol. Med. 143, (1973) serve as a useful guide.

The substance is preferably administered orally, but parenteral routes such as subcutaneously, intramuscularly, intravenously or intraperitoneally can also be employed.

The compounds of this invention can be utilized to achieve the reduction of blood pressure by formulating in compositions such as tablets, capsules or elixirs for oral administration or in sterile solution or suspensions for parenteral administration. About 10 to 500 mg. of a compound or mixture of compounds of formula I or physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention. All temperatures are in degrees celsius.

EXAMPLE 1

3-Acetylthio-2-methoxycarbonylmethylpropanoic acid

A mixture of thiolacetic acid (12.5 g.) and 3-methoxycarbonyl-2-methylenepropanoic acid (17.1 g.) are heated on the steam bath for two hours. The reaction is concentrated in vacuo and the residue is dissolved in ethyl acetate (125 ml.) and dicyclohexylamine (35 ml.) is added. The crystals are filtered, dried and recrystallized from ethyl acetate to yield 37.8 g., m.p. 120°–121°. This dicyclohexylammonium salt of 3-acetylthio-2-methoxycarbonylmethylpropanoic acid is converted to the free acid by distribution between a system of ethyl acetate and 10% aqueous potassium bisulfate.

EXAMPLE 2

1-[3-(Acetylthio)-2-(methoxycarbonylmethyl)-propanoyl]-L-proline tert-butyl ester To a solution of L-proline tert-butyl ester (1.71 g.) and 3-hydroxybenzotriazole (1.35 g.) in dichloromethane (15 ml.), dicyclohexylcarbodiimide (2.06 g.) and 3-acetylthio-2-methoxycarbonylmethylpropanoic acid (2.2 g.) are added. After 18 hours stirring at room temperature, the precipitate formed is filtered off, the filtrate is washed neutral, dried, and concentrated to dryness to yield 3.7 g. of 1-[3-(acetylthio)-2-(methoxycarbonylmethyl)-propanoyl]-L-proline tert-butyl ester Rf: 0.8 (silica gel-ethyl acetate).

EXAMPLE 3

1-[3-(Acetylthio)-2-(methoxycarbonylmethyl)-propanoyl]-L-proline

1-[3-(Acetylthio)-2-(methoxycarbonylmethyl)-propanoyl]-L-proline tert-butyl ester (2.9 g.) is dissolved in a mixture of trifluoroacetic acid (17.5 ml.) and anisole (8.4 ml.). After one hour storage at room temperature the excess trifluoroacetic acid is removed in vacuo and the residue is precipitated twice from ether-hexane to yield 2.1 g. of 1-[3-(acetylthio)-2-(methoxycarbonylmethyl)-propanoyl]-L-proline Rf: $\neq$ 0.4 (silica gel-benzene:acetic acid 75:25).

EXAMPLE 4

1-[3-Mercapto-2-(methoxycarbonylmethyl)propanoyl]-L-proline

1-[3-(Acetylthio)-2-(methoxycarbonylmethyl)-propanoyl]-L-proline (2.1 g.) is dissolved in a mixture of water (35 ml.) and concentrated ammonia (35 ml.) under a blanket of argon. After twenty minutes, the solution is chilled in an ice bath, made acidic with concentrated hydrochloric acid, saturated with sodium chloride and extracted with ethyl acetate. The organic layer is dried and concentrated to dryness in vacuo to yield 1.1 g. of 1-[3-mercapto-2-(methoxycarbonylmethyl)propanoyl]-L-proline that is purified by chromatography on silica gel (benzene:acetic acid 75:25). $R_f$ 0.35 (silica gel, benzene:acetic acid, 75:25).

EXAMPLE 5

1-[2-Carboxymethyl-3-mercaptopropanoyl]-L-proline

To a solution of 1-[3-(acetylthio)-2-(methoxycarbonylmethyl)propanoyl]-L-proline (3 g.) in methanol (60 ml.), N sodium hydroxide (60 ml.) is added. After four hours, the solution is applied to a column of Dowex 50 ion exchange resin in the hydrogen cycle, and the desired material is eluted with water to yield 2.3 g. of 1-[2-carboxymethyl-3-mercaptopropanoyl]-L-proline $R_f$ 0.2 (silica gel, benzene:acetic acid 75:25).

EXAMPLE 6

1-[2-Carbamoylmethyl-3-mercaptopropanoyl]-L-proline (A) 1-[3-(Acetylthio)-2-(methoxycarbonylmethyl)-propanoyl]-L-proline (2.1 g.) is dissolved in a mixture of water (40 ml.) and concentrated ammonia (40 ml.). After one hour the reaction mixture is concentrated to ⅓ volume, and applied to a column of Dowex 50 resin in the hydrogen cycle. The product is eluted with water. The aqueous is extracted with ethyl acetate and then concentrated to dryness to yield 1.4 g. of 1-[2-carbamoylmethyl-3-mercaptopropanoyl]-L-proline $R_f$ 0.50 (silica gel, chloroform:methanol:acetic acid:water).

(B) 1-[2-Carbamoylmethyl-3-acetylthiopropanoyl]-L-proline (1.2 g.) is dissolved in a mixture of water (20 ml.) and concentrated ammonia (20 ml.). After 15 minutes the reaction mixture is processed as described in "A" above to obtain 1-[2-carbamoylmethyl-3-mercaptopropanoyl]-L-proline.

EXAMPLE 7

3-Acetylthio-2-carbamoylmethylpropanoic acid

By substituting 3-carbamoyl-2-methylenepropanoic acid for the 3-methoxycarbonyl-2-methylenepropanoic acid in the procedure of Example 1, 3-acetylthio-2-carbamoylmethylpropanoic acid is obtained, m.p. 110°–111°.

EXAMPLE 8

3-Acetylthio-2-cyanomethylpropanoic acid

Dicyclohexylcarbodiimide (1.03 g.) is added to a solution of 3-acetylthio-2-carbamoylmethylpropanoic acid (1.02 g.) in pyridine (18 ml.). After five hours stirring at room temperature, the precipitate is filtered off and the filtrate is concentrated in dryness, the residue is dissolved in ethyl acetate and extracted with saturated aqueous bicarbonate. The aqueous phase is acidified and extracted with ethyl acetate. This organic layer is dried and concentrated to dryness. The residue, 3-acetylthio-2-cyanomethylpropanoic acid is crystallized from ether-hexane, m.p. 110°–112°.

EXAMPLE 9

3-Acetylthio-2-(methoxycarbonylmethyl)propanoic acid N-hydroxysuccinimido ester

To a solution of 3-acetylthio-2-(methoxycarbonylmethyl-propanoic acid (5.5 g.) and N-hydroxysuccinimide (2.9 g.) in tetrahydrofuran (100 ml.) chilled in an ice bath, dicyclohexylcarbodiimide (5.15 g.) is added. The reaction mixture is stirred for 15 hours at 5°, filtered and the filtrate is concentrated to dryness in vacuo to yield 3-acetylthio-2-(methoxycarbonylmethyl)-propanoic acid N-hydroxysuccinimido ester.

EXAMPLE 10

1-[2-(Carbamoylmethyl)-3-(acetylthio)propanoyl]-L-proline

By substituting 3-acetylthio-2-(carbamoylmethyl)-propanoic acid for the 3-(acetylthio)-2-(methoxycarbonylmethyl)-propanoic acid in the procedure of Example 2, and then submitting the product to the procedure of Example 3, 1-[2-(carbamoylmethyl)-3-(acetylthio)-propanoyl]-L-proline tert-butyl ester and 1-[2-(carbamoylmethyl)-3-(acetylthio)-propanoyl]-L-proline are obtained.

EXAMPLE 11

3-Acetylthio-2-[(N-butylcarbamoyl)methyl]propanoic acid

By substituting 3-(N-butylcarbamoyl)-2-methylenepropanoic acid for the 3-methoxycarbonyl-2-methylenepropanoic acid in the procedure of Example 1, 3-acetylthio-2-[(N-butylcarbamoyl)methyl]propanoic acid is obtained.

EXAMPLE 12

1-[3-(Acetylthio)-2-[(N-butylcarbamoyl)methyl]propanoyl-L-proline

By substituting 3-(acetylthio)-2-[(N-butylcarbamoyl)methyl]propanoic acid for the 3-(acetylthio)-2-(methoxycarbonylmethyl)propanoic acid in the procedure of Example 2 and then submitting the product to the procedure of Example 3, 1-[3-(acetylthio)-2-[N-butylcarbamoyl]methyl]-propanoyl-L-proline is obtained.

EXAMPLE 13

2-Methylene-4-(ethoxycarbonyl)butyric acid

A mixture of 2-methyleneglutaric acid [Ber. 34, 427 (1901)] (40 g.) and acetyl chloride (80 ml.) is heated on the steam bath for 1.5 hours. The excess acetyl chloride is removed in vacuo (75°) and the residue is evaporated from toluene twice. Finally, the residue is dissolved in ethanol and heated on the steam bath for one hour. The reaction mixture is concentrated to dryness to yield 2-methylene-4-(ethoxycarbonyl)butyric acid.

EXAMPLE 14

1-[2-Mercaptomethyl-4-(ethoxycarbonyl)butanoyl]-L-proline

By substituting 2-methylene-4-(ethoxycarbonyl)butyric acid for the 3-methoxycarbonyl-2-methylenepropanoic acid in the procedure of Example 1, and then submitting the product to the procedure of Examples 2, 3 and 4, 2-acetylthiomethyl-4-(ethoxycarbonyl)butyric acid, 1-[2-(acetylthio)methyl-4-(ethoxycarbonyl)butanoyl]-L-proline tert-butyl ester, 1-[2-(acetylthiomethyl)-4-(ethoxycarbonyl)-butanoyl]-L-proline and 1-[2-mercaptomethyl-4-(ethoxycarbonyl)butanoyl]-L-proline are obtained.

EXAMPLE 15

1-[3-Mercapto-2-(cyanomethyl)propanoyl]-L-proline

By substituting 3-acetylthio-2-cyanomethylpropanoic acid for the 3-(acetylthio)-2-(methoxycarbonylmethyl)propanoic acid in the procedure of Example 2, and then submitting the product to the procedures of Examples 3 and 4, 1-[3-(acetylthio)-2-(cyanomethyl)propanoyl]-L-proline tert-butyl ester, 1-[3-(acetylthio)-2-(cyanomethyl)propanoyl]-L-proline and 1-[3-mercapto-2-(cyanomethyl)propanoyl]-L-proline are obtained.

By treating this product with an equivalent proportion of sodium hydroxide solution, then removing the water by freeze drying, the sodium salt is obtained.

EXAMPLE 16

1,1′-[Dithiobis-[2-(methoxycarbonylmethyl)-3-propanoyl]]-bis-L-proline

To a solution of 1-[3-mercapto-2-(methoxycarbonylmethyl)-propanoyl]-L-proline (1 g.) in water (20 ml.), an alcoholic solution of iodine is added until persistent yellow color, while maintaining the pH between 5 and 7 by careful addition of N sodium hydroxide. The yellow color is discharged by addition of a few drops of aqueous sodium thiosulfate and after acidification with concentrated hydrochloric acid, the reaction mixture is extracted with ethyl acetate. The organic layer is dried and concentrated to dryness in vacuo to yield 1,1′-[dithiobis-[2-(methoxycarbonylmethyl)-3-propanoyl]]-bis-L-proline.

EXAMPLE 17

$N^\alpha$-[3-(Acetylthio)-2-(methoxycarbonylmethyl)-propanoyl]-L-arginine

A solution of 3-(acetylthio)-2-(methoxycarbonylmethyl)-propanoic acid N-hydroxysuccinimide ester (1.67 g.) in ethanol (17 ml.) is added dropwise to a solution of L-arginine (0.9 g.), and sodium bicarbonate (1.26 g.) in water (12 ml.). The mixture is stirred at room temperature for 16 hours, and then extracted with ethyl acetate. The aqueous layer is applied to a column of Dowex 50 resin in the hydrogen cycle, and eluted with water until no more acidic material is eluted. $N^\alpha$-[3-(acetylthio)-2-(methoxycarbonylmethyl)-propanoyl]]-L-arginine is then eluted with pyridine-acetate buffer at pH 6.5.

EXAMPLE 18

$N^\alpha$-[3-Mercapto-2-(methoxycarbonylmethyl)-propanoyl]-L-arginine

To a solution of $N^\alpha$-[3-(acetylthio)-2-(methoxycarbonylmethyl)propanoyl]-L-arginine (1.9 g.) in methanol (10 ml.), sodium methoxide (0.56 g.) is added. After ten minutes, the solution is applied to a column of Dowex 50 resin and the column is washed with water until no more acidic material is eluted. $N^\alpha$-[3-mercapto-2-(methoxycarbonylmethyl)propanoyl]-L-arginine is then eluted with a pyridine-acetate buffer of pH 6.5.

EXAMPLE 19

$N^\alpha$-[3-Mercapto-2-(carbamoylmethyl)propanoyl]-L-arginine

By substituting $N^\alpha$-[3-(acetylthio)-2-(methoxycarbonylmethyl)propanoyl]-L-arginine for the 1-[3-(acetylthio)-2-(methoxycarbonylmethyl)propanoyl]-L-proline in the procedure of Example 6A, and then isolating the product with Dowex 50 resin as described in the procedure of Example 17, $N^\alpha$-[3-mercapto-2-(carbamoylmethyl)propanoyl]-L-arginine is obtained.

EXAMPLE 20

$N^\alpha$-[3-Mercapto-2-(methoxycarbonylmethyl)-propanoyl]-L-histidine

By substituting L-histidine for the L-arginine in the procedure of Example 17, and then submitting the product to the procedure of Example 18, $N^\alpha$-[3-(acetylthio)-2-methoxycarbonylmethyl)propanoyl]-L-histidine and $N^\alpha$-[3-mercapto-2-(methoxycarbonylmethyl)-propanoyl]-L-histidine are obtained.

EXAMPLE 21

$N^\alpha$-[3-Mercapto-2-(carbamoylmethyl)propanoyl]-L-histidine

By substituting $N^\alpha$-[3-(acetylthio)-2-methoxycarbonylmethyl)propanoyl]-L-histidine for the $N^\alpha$-[3-(acetylthio)-2-(methoxycarbonylmethyl)propanoyl]-L- arginine in the procedure of Example 19, $N^\alpha$-[3-mercapto-2-(carbamoylmethyl)-propanoyl]-L-histidine is obtained.

EXAMPLE 22

N-[3-Mercapto-2-(methoxycarbonylmethyl)-propanoyl]-L-alanine

By substituting L-alanine tert-butyl ester for the L-proline tert-butyl ester in the procedure of Example 2, and then submitting the product to the procedure of Examples 3 and 4, N-[3-mercapto-2-(methoxycarbonylmethyl)-propanoyl]-L-alanine is obtained.

EXAMPLE 23

N-[2-(Carbamoylmethyl)-3-mercaptopropanoyl]-L-alanine

By substituting L-alanine tert-butyl ester for the L-proline tert-butyl ester in the procedure of Example 2, and then submitting the product to the procedures of Examples 3 and 6, N-[2-(carbamoylmethyl)-3-mercaptopropanoyl]-L-alanine is obtained.

EXAMPLE 24

N-[3-Mercapto-2-(methoxycarbonylmethyl)-propanoyl]-L-asparagine

By substituting L-asparagine tert-butyl ester for the L-proline tert-butyl ester in the procedure of Example 2, and then submitting the product to the procedure of Examples 3 and 4 N-[3-mercapto-2-(methoxycarbonylmethyl)propanoyl]-L-asparagine is obtained.

EXAMPLE 25

N-[2-(Carbamoylmethyl)-3-mercaptopropanoyl]-L-glutamine

By substituting L-glutamine tert-butyl ester for the L-proline tert-butyl ester in the procedure of Example 2, and then submitting the product to the procedures of Examples 3 and 6A, N-[2-(carbamoylmethyl)-3-mercaptopropanoyl]-L-glutamine is obtained.

EXAMPLE 26

N-[3-Mercapto-2-(methoxycarbonylmethyl)-propanoyl]-L-aspartic acid

By substituting L-aspartic acid di-tert-butyl ester for the L-proline tert-butyl ester in the procedure of Example 2, and then submitting the product to the procedure of Examples 3 and 4, N-[3-mercapto-2-(methoxycarbonylmethyl)propanoyl]-L-aspartic acid is obtained.

EXAMPLE 27

N-[2-(Carbamoylmethyl)-3-mercaptopropanoyl]-L-glutamic acid

By substituting L-glutamic acid di-tert-butyl ester for the L-proline tert-butyl ester in the procedure of Example 2, and then submitting the product to the procedure of Examples 3 and 6A, N-[2-(carbamoylmethyl)-3-mercaptopropanoyl]-L-glutamic acid is obtained.

EXAMPLE 28

N-[3-(Acetylthio)-2-(methoxycarbonylmethyl)-propanoyl]-S-(N-ethylcarbamoyl)-L-cysteine A solution of 3-(acetylthio)-2-(methoxycarbonylmethyl)-propanoic acid N-hydroxysuccinimido ester (1.67 g.) in ethanol (17 ml.) is added dropwise to a solution of S-(N-ethylcarbamoyl)-L-cysteine (1 g.) and sodium bicarbonate (1.26 g.) in water (12 ml.). The mixture is stirred at room temperature for sixteen hours and then is extracted with ethyl acetate. The aqueous layer is acidified and extracted with ethyl acetate. This second organic layer is dried and concentrated to dryness in vacuo to yield N-[3-(acetylthio)-2-(methoxycarbonylmethyl)propanoyl]-S-(N-ethylcarbamoyl)-L-cysteine.

EXAMPLE 29

N-[3-Mercapto-2-(methoxycarbonylmethyl)-propanoyl]-L-cysteine

To a solution of N-[3-(acetylthio)-2-(methoxycarbonylmethyl)propanoyl]-S-(N-ethylcarbamoyl)-L-cysteine (1.9 g.) in methanol (10 ml.), sodium methoxide (0.84 g.) is added. After thirty minutes, the solution is diluted with 0.1 N hydrochloric acid and extracted with ethyl acetate. The organic layer is dried and concentrated to dryness in vacuo to yield N-[3-mercapto-2-(methoxycarbonylmethyl)propanoyl]-L-cysteine.

EXAMPLE 30

$N^\alpha$-[3-(Acetylthio)-2-(methoxycarbonylmethyl)-propanoyl]-L-lysine

By substituting $N^\epsilon$-tert-butyloxycarbonyl-L-lysine tert-butyl ester for the L-proline tert-butyl ester in the procedure of Example 3, followed by isolation with Dowex 50 resin as described in Example 17, $N^\alpha$-[3-(acetylthio)-2-(methoxycarbonylmethyl)propanoyl]-L-lysine is obtained.

EXAMPLE 31

$N^\alpha$-[3-Mercapto-2-(methoxycarbonylmethyl)-propanoyl]-L-lysine

By substituting $N^\alpha$-[3-(acetylthio)-2-(methoxycarbonylmethyl)propanoyl]-L-lysine for the $N^\alpha$-[3-(acetylthio)-2-(methoxycarbonylmethyl)propanoyl]-L-arginine in the procedure of Example 18, $N^\alpha$-[3-mercapto-2-(methoxycarbonylmethyl)propanoyl]-L-lysine is obtained.

EXAMPLE 32

$N^\alpha$-[2-(Carbamoylmethyl)-3-mercaptopropanoyl]-L-lysine

By substituting $N^\alpha$-(3-(acetylthio)-2-methoxycarbonylmethylpropanoyl]-L-lysine for the $N^\alpha$-[3-acetylthio-2-methoxycarbonylmethylpropanoyl]-L-arginine in the procedure of Example 19, $N^\alpha$-[2-(carbamoylmethyl)-3-mercaptopropanoyl]-L-lysine is obtained.

EXAMPLE 33

N-[3-Mercapto-2-(methoxycarbonylmethyl)-propanoyl]-L-methionine

By substituting L-methionine diphenylmethyl ester for the L-proline tert-butyl ester in the procedure of Example 2, and then submitting the product to the procedure of Examples 3 and 4, N-[3-mercapto-2-(methoxycarbonylmethyl)propanoyl]-L-methionine is obtained.

EXAMPLE 34

N-[2-(Carbamoylmethyl)-3-mercaptopropanoyl]-L-methionine

By substituting L-methionine diphenylmethyl ester for the L-proline tert-butyl ester in the procedure of Example 2, and then submitting the product to the procedure of Examples 3 and 6A, N-[2-(carbamoylmethyl)-3-mercaptopropanoyl]-L-methionine is obtained.

EXAMPLE 35

N-[3-Mercapto-2-(methoxycarbonylmethyl)-propanoyl]-L-phenylalanine

By substituting L-phenylalanine tert-butyl ester for the L-proline tert-butyl ester in the procedure of Example 2, and then submitting the product to the procedure of Examples 3 and 4, N-[3-mercapto-2-(methoxycarbonylmethyl)propanoyl]-L-phenylalanine is obtained.

EXAMPLE 36

N-[2-(Carbamoylmethyl)-3-mercaptopropanoyl]-L-phenylalanine

By substituting L-phenylalanine tert-butyl ester for the L-proline tert-butyl ester in the procedure of Example 2, and then submitting the product to the procedure of Examples 3 and 6A, N-[2-(carbamoylmethyl)-3-mercaptopropanoyl]-L-phenylalanine is obtained.

EXAMPLE 37

1-[3-Mercapto-2-(methoxycarbonylmethyl)propanoyl]-4-hydroxy-L-proline

By substituting 4-hydroxy-L-proline p-methoxybenzyl ester for the L-proline tert-butyl ester in the procedure of Example 2, and then submitting the product to the procedures of Examples 3 and 4, 1-[3-mercapto-2-(methoxycarbonylmethyl)propanoyl]-4-hydroxy-L-proline is obtained.

EXAMPLE 38

1-[2-Carbamoylmethyl-3-mercaptopropanoyl]-5-hydroxy-L-pipecolic acid

By substituting 5-hydroxy-L-pipecolic acid for the S-(N-ethylcarbamoyl)-L-cysteine in the procedure of Example 28, and then submitting the product to the procedure of Example 6A, 1-[2-carbamoylmethyl-3-mercaptopropanoyl]-5-hydroxy-L-pipecolic acid is obtained.

EXAMPLE 39

1-[3-Mercapto-2-(methoxycarbonylmethyl)propanoyl]-L-pipecolic acid

By substituting L-pipecolic acid tert-butyl ester (prepared from L-pipecolic acid as described for L-proline) for the L-proline tert-butyl ester in the procedure of Example 2, and then submitting the product to the procedure of Examples 3 and 4, 1-[3-mercapto-2-(methoxycarbonylmethyl)-propanoyl]-L-pipecolic acid is obtained.

EXAMPLE 40

N-[3-Mercapto-2-(methoxycarbonylmethyl)-propanoyl]-L-serine

By substituting O-tert-butyl-L-serine tert-butyl ester for the L-proline tert-butyl ester in the procedure of Example 2, and then submitting the product to the procedure of Examples 3 and 4, N-[3-mercapto-2-(methoxycarbonylmethyl)-propanoyl]-L-serine is obtained.

EXAMPLE 41

N-[2-(Carbamoylmethyl)-3-mercaptopropanoyl]-L-threonine

By substituting O-tert-butyl-L-threonine tert-butyl ester for the L-proline tert-butyl ester in the procedure of Example 2, and then submitting the product to the procedures of Examples 3 and 6A, N-[2-(carbamoylmethyl)-3-mercaptopropanoyl]-L-threonine is obtained.

EXAMPLE 42

N-[3-Mercapto-2-(methoxycarbonylmethyl)-propanoyl]-L-tyrosine

By substituting L-tyrosine for the S-(N-ethylcarbamoyl)-L-cysteine in the procedure of Example 28, and then submitting the product to the procedure of Example 29, N-[3-mercapto-2-(methoxycarbonylmethyl)propanoyl]-L-tyrosine is obtained.

EXAMPLE 43

$N^\alpha$-[3-Mercapto-2-(methoxycarbonylmethyl)-propanoyl]-L-tryptophane

By substituting L-tryptophane for the S-(N-ethylcarbamoyl)-L-cysteine in the procedure of Example 28, and then submitting the product to the procedure of Example 29, $N^\alpha$-[3-mercapto-2-(methoxycarbonylmethyl)propanoyl]-L-tryptophane is obtained.

EXAMPLE 44

$N^\alpha,N^\alpha$-[Dithiobis-(2-methoxycarbonylmethyl)-3-propanoyl]-bis-L-lysine By substituting $N^\alpha$-[3-mercapto-2-(methoxycarbonylmethyl)propanoyl]-L-lysine for the 1-[3-mercapto-2-(methoxycarbonylmethyl)propanoyl]-L-proline in the procedure of Example 16, and isolating the product with a Dowex 50 resin as described in the procedure of Example 18, $N^\alpha,N^\alpha$-[dithiobis-(2-methoxycarbonylmethyl)-3-propanoyl]-bis-L-lysine is obtained.

EXAMPLE 45

1-[2-(Benzoylthio)-3-(methoxycarbonyl)propanoyl]-L-proline

L-Proline (5.75 g.) is dissolved in aqueous N sodium hydroxide (50 ml.) and the solution is chilled in an ice bath with stirring. 2N Sodium hydroxide (25 ml.) and 2-bromo-3-(methoxycarbonyl)propionyl chloride (11.6 g.) are added in that order and the mixture is removed from the ice bath and stirred at room temperature for one hour. A mixture of thiobenzoic acid (7.5 g.) and potassium carbonate (4.8 g.) in water (50 ml.) is added and the mixture is stirred overnight at room temperature. After acidification with concentrated hydrochloric acid, the aqueous solution is extracted with ethyl acetate and the organic phase is washed with water, dried and concentrated to dryness to give 1-[2-(benzoylthio)-3-(methoxycarbonyl)propanoyl]-L-proline.

EXAMPLE 46

1-[2-Mercapto-3-(methoxycarbonylmethyl)propanoyl]-L-proline

By substituting 1-[2-(benzoylthio)-3-(methoxycarbonyl]propanoyl-L-proline for the 1-[3-(acetylthio)-2-(methoxycarbonylmethyl)propanoyl]-L-proline in the procedure of Example 4, 1-[2-mercapto-3-(methoxycarbonylmethyl)propanoyl]-L-proline is obtained.

EXAMPLE 47

N-[3-Mercapto-2-(methoxycarbonylmethyl)-propanoyl]-N-methyl-L-phenylalanine

By substituting N-methyl-L-phenylalanine for the S-(N-ethylcarbamoyl)-L-cysteine in the procedure of Example 28, and then submitting the product to the procedure of Example 29, N-[3-mercapto-2-(methoxycarbonylmethyl)propanoyl]-N-methyl-L-phenylalanine is obtained.

EXAMPLE 48

1-[3-Acetylthio-2-(cyanomethyl)propanoyl]-L-proline

1-[3-Acetylthio-2-(cyanomethyl)propanoyl]-L-proline tert butyl ester (2.1 g.) and p-toluene sulfonic acid (0.500 g.) are dissolved in benzene (25 ml.) and the solution is refluxed for 30 minutes. The solvent is removed in vacuo, the residue is dissolved in ethyl acetate, washed twice with water, dried and concentrated to dryness. The residue is chromatographed on silica gel with benzene:acetic acid (75:25), yield 0.85 g. $R_f$ 0.18 (silica gel:benzene:acetic acid 75:25).

What is claimed is:

1. A compound of the formula

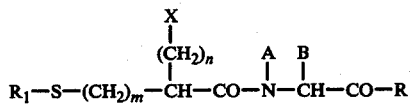

and salts thereof,
wherein R is hydroxy or lower alkoxy;
$R_1$ is hydrogen, lower alkanoyl, benzoyl or

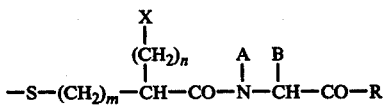

A is hydrogen, lower alkyl or hydroxy-lower alkylene;
B is hydrogen, lower alkyl, hydroxy-lower alkylene, amino-lower alkylene, guanidino-lower alkylene, mercapto-lower alkylene, lower alkylthio-lower alkylene, carbamoyl-lower alkylene or carboxy-lower alkylene;
X is carboxy, lower alkoxycarbonyl, carbamoyl, N-substituted carbamoyl wherein the N-substituent is lower alkyl or phenyl-lower alkylene, or cyano;
m is 0 or 1; and
n is 0, 1, 2, 3 or 4.

2. A compound as in claim 1 wherein R is hydroxy; $R_1$ is hydrogen or lower alkanoyl; X is lower alkoxycarbonyl or carbamoyl; A is hydrogen; B is lower alkyl or amino-lower alkylene; m is 1 and n is 1 or 2.

3. A compound as in claim 1 wherein

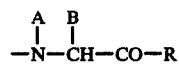

is the radical of glycine, alanine, leucine, threonine, lysine, arginine, glutamine, methionine, serine, cysteine, valine, asparagine or glutamic acid.

4. A compound as in claim 1 wherein $R_1$ is

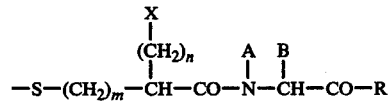

5. A compound as in claim 1 wherein X is lower alkoxycarbonyl.

6. A compound as in claim 1 wherein X is carbamoyl.

7. A compound as in claim 1 wherein R is hydroxy; A and $R_1$ each is hydrogen; B is carboxymethylene; X is methoxycarbonyl; and m and n each is 1.

8. A compound as in claim 1 wherein R is hydroxy; A and $R_1$ each is hydrogen; B is methyl; X is carbamoyl; and m and n each is 1.

9. A compound as in claim 1 wherein R is hydroxy; A and $R_1$ each is hydrogen; B is 4-aminobutyl; X is methoxycarbonyl; and m and n each is 1.

10. A compound as in claim 1 wherein R is hydroxy; A and $R_1$ each is hydrogen; B is methyl; X is methoxycarbonyl; and m and n each is 1.

* * * * *